United States Patent [19]

Townsend et al.

[11] 3,960,864

[45] June 1, 1976

[54] METHOD OF SYNTHESIZING 1-(TETRAHYDRO-2-FURANYL)-5-FLUOROURACIL

[75] Inventors: Leroy B. Townsend; Robert A. Earl, both of Salt Lake City; Steven J. Manning, Bountiful, all of Utah

[73] Assignee: Th University of Utah, Salt Lake City, Utah

[22] Filed: May 6, 1974

[21] Appl. No.: 467,538

[52] U.S. Cl. ............................................. 260/260
[51] Int. Cl.² ...................................... C07D 239/54
[58] Field of Search ................................... 260/260

[56] References Cited
FOREIGN PATENTS OR APPLICATIONS
1,168,391  10/1969  United Kingdom................. 260/260

OTHER PUBLICATIONS

Earl et al., Journal of Heterocyclic Chemistry 9, 1141 (1972).

*Primary Examiner*—Paul M. Coughlan, Jr.

[57] ABSTRACT

An improved method for synthesizing 1-(tetrahydro - 2-furanyl) - 5-fluorouracil from a silyl derivitive of 5-fluorouracil (bis - trimethylsilyl 5-fluorouracil) by reacting the same with 2-chlorotetrahydrofuran. The reaction is carried out at controlled conditions of temperature and under an inert gas. Yields in excess of 80% of the theoretical are obtained as calculated upon the starting amounts of 5-fluorouracil.

8 Claims, No Drawings

METHOD OF SYNTHESIZING 1-(TETRAHYDRO-2-FURANYL)-5-FLUOROURACIL

BACKGROUND

1. Field of the Invention

The present invention relates to an improved method for synthesizing 1-(tetrahydro - 2-furanyl) - 5-fluorouracil.

2. The Prior Art

The synthesis of 1-(tetrahydro - 2-furanyl) -5-fluorouracil has been reported in the literature and is the subject of at least one patent by Solomon A. Giller (British Patent No. 1,168,391). The method of synthesis disclosed by Giller involves, in part, the use of mercury compounds of uracils; however, the synthesis method of interest herein is that set forth in examples 8 and 9 on page 4 of the above British patent.

In example 8, 5-fluorouracil and chlorotrimethylsilane are stirred in the presence of triethylamine in dry toluene. The precipitated triethylamine hydrochloride is filtered off and the filtrate is concentrated and reacted with 2-chlorofuranidine to produce 1-(tetrahydro - 2-furanyl) - 5-fluorouracil. In example 9, Hexamethyldisilazane is used in place of the chlorotrimethylsilane of example 8. In both example 8 and 9 above, hydrogen chloride is produced as a by-product of the reaction and tends to cleave certain bonds of the starting material, bis-trimethylsilyl -5-fluorouracil, and the product, 1-(tetrahydro 2-furanyl) - 5-fluorouracil, thus acting as one of the contributory factors for the relatively low percentages of theoretical yields 50% and 65%, respectively.

The product of interest herein, 1-(tetrahydro - 2-furanyl) - 5-fluorouracil, has been reported as an antimetabolite which possesses a relatively high therapeutic index (approximately two times that of 5-fluorouracil) and low toxicity (approximately 5 to 6 times less than 5-fluorouracil) toward cancer of the breast and gastrointestinal tract. See "The Synthesis of 1-(tetrahydro -2-furanyl) -5-fluorouracil (Ftorafur) via Direct Fluorination", R. A. Earl and L. B. Townsend, *Journal of Heterocyclic Chemistry* 9, 1141 (1972).

Due to the interest in this particular compound, it has been synthesized as set forth in the British patent, as previously discussed, and also by an alternate synthesis route using the direct fluorination of 1-(tetrahydro - 2-furanyl) uracil as set forth in the above publication of Earl and Townsend. The former synthetic route results in relatively low yields and the latter synthetic route involves the use of a gas, trifluoromethylhypofluorite, which is highly reactive, with a number of potential hazards. Extreme difficulties in scaling up the latter process, to produce large quantities of 1-(tetrahydro -2-furanyl) - 5-fluorouracil may thus be encountered. Scale up will be desirable if this compound successfully passes the necessary tests to thereby be accepted as an approved chemotherapeutic agent against certain forms of cancer.

Accordingly, it would be a significant advance in the art to provide an improved method of synthesizing 1-(tetrahydro - 2-furanyl) - 5-fluorouracil from commercially available compounds. The present invention provides this advance.

BRIEF SUMMARY AND OBJECTS OF THE INVENTION

The present invention involves the synthesis of 1-(tetrahydro-2-furanyl) - 5-fluorouracil by reacting bis-trimethylsilyl 5-fluorouracil with 2-chlorotetrahydrofurane in cold methylene chloride and in the presence of molecular sieves. The bis-trimethylsilyl 5-fluorouracil is prepared by the silylation of 5-fluorouracil with hexamethyldisilizane. An inert atmosphere for the reaction is assured by flushing the entire system throughout the reaction with an inert gas such as nitrogen.

It is therefore a primary object of this invention to provide an improved method for the production of 1-(tetrahydro - 2-furanyl) - 5-fluorouracil.

It is another object of this invention to produce 1-(tetrahydro - 2furanyl) - 5-fluorouracil, by reacting the bis-trimethylsilyl derivative of 5-fluorouracil, bis-trimethylsilyl-5-fluorouracil, with 2-chlorotetrahydrofuran.

It is an even still further object of this invention to provide an improved method for synthesizing 1-(tetrahydro -2-furanyl) - 5-fluorouracil, the method accommodating an improved technique for increasing the percentage of yield.

These and other objects and features of the present invention will become more fully apparent from the following description and appended claims.

DETAILED DESCRIPTION OF THE INVENTION

The compound of this invention, 1-(tetrahydro - 2-furanyl) - 5-fluorouracil, is prepared by reacting the bis-trimethyl silyl derivative of 5-fluorouracil under very cold conditions with 2-chlorotetrahydrofuran and in the presence of cold methylene chloride or similar solvent and molecular sieves. This compound is the subject of the previously described British patent and is considered to be an antimetabolite useful as a therapeutic agent under certain circumstances as set forth in the subject patent.

In one presently preferred embodiment of this invention, a four-necked round bottom flask (5,000 ml) was fitted with a mechanical stirrer, gas inlet and outlet tubes, and an addition funnel with drying tube. The foregoing equipment was previously dried in an oven prior to assembly and thereafter fitted with a low temperature thermometer. A nitrogen atmosphere for the reaction was assured by adjusting a slow stream of nitrogen gas to purge the assembled apparatus. Nitrogen gas flow was continued through the apparatus throughout the entire reaction.

The bis-trimethylsilyl -5-fluorouracil was prepared by adding 500 grams of 5-fluorouracil, previously dried in a vacuum oven to remove traces of water, to 2,300 ml. of hexamethyldisilizane. The mixture was refluxed for four hours, at which time all of the solid 5-fluorouracil had dissolved. The excess hexamethyldisilizane was then removed under vacuum with the final pot temperature and pressure being 60°C and 2 mm Hg, respectively.

Preparation of the bis-trimethylsilyl 5-fluorouracil immediately prior to the reaction with 2-chlorotetrahydrofuran is necessary due to the extreme instability of the compound. The bis-trimethylsilyl -5-fluorouracil thus prepared was then transferred to the reaction flask, although for sake of convenience the silyation reaction may also be carried out in the reaction flask. This was followed by the addition to the flask of an equal volume, approximately, of dry methylene chloride and 70 grams of molecular sieves. The presence of molecular sieves is very important since they serve two purposes: one, to remove traces of water from the reaction solution and two, to remove any HCl that may arise from the decomposition of 2-chlorotetrahydrofuran. Molecular sieves are commercially available and the 4A size was used for this procedure.

Stirring was commenced and the flask and contents thereof cooled to below −65°C and above the freezing point of the solvent in a dry ice/acetone bath. It should be noted that there is some tendency for the bis-trimethylsilyl deriivitive to crystallize during cooling. If this happens, additional cold, dry methylene chloride should be added to effect solution.

In a separate container, 430 grams, representing an approximate 5% molar excess, of 2-chlorotetrahydrofuran was mixed with an equal amount of dry, methylene chloride and stirred with an additional quantity of molecular sieves, approximately 15 grams. This mixture was cooled to about −78°C and was gradually added to the flask from a dropping funnel at such a rate so as to maintain the internal temperature of the reaction solution to below about −65°C and above the freezing point of the solvent. Cooling the reaction flask in a dry ice/acetone bath was continued throughout the reaction. Due to the exothermic nature of the reaction, slow addition of one reactant into the other, coupled with continued cooling, assures maintenance of the temperature at the desired low level.

After the addition, the reaction solution was allowed to slowly warm to room temperature under continuous stirring until the reaction was complete. If desired, progress of the reaction may be followed by conventional thin layer chromatographic techniques.

Once the reaction was completed, approximately two hours, the reaction solution was again cooled to approximately −78°C with the dry ice/acetone bath. The cooled reaction solution was then added by dropwise addition from a dropping funnel to a basic solution of ammonium hydroxide in methanol which had also been previously cooled to approximate −70°C. Dropwise addition and continuous cooling are required due to the very exothermic nature of the reaction and the need to maintain a relatively cold reaction solution, preferably below about −10°C. Cooling in the dry ice/acetone cooling bath was continued throughout the addition.

During the addition, the reaction solution was poured through a glasswool mat in the dropping funnel to remove the molecular sieves. The foregoing basic solution was prepared by adding ammonium hydroxide to methanol, for example, 420 ml. of 58% ammonium hydroxide, 28–30% ammonia, in 1250 ml. methanol; however, since it is important that the pH of the solution be maintained above about 7.5 until all of the reaction solution has been added, the addition of additional quantities of ammonium hydroxide may be necessary.

After the reaction solution had been added to the basic solution the combined solution was allowed to warm to room temperature while stirring was continued for at least one hour. It is during this phase of the reaction that the product, 1-(tetrahydro - 2-furanyl) -5-fluorouracil, precipitates from the solution. Certain impurities are also carried out of solution with the product.

A weak acid, which in this preferred embodiment constituted dry ice, ($CO_2$), was then added to the precipitate/solution slurry until the pH was again adjusted to 7.5. Liquids capable of volatilizing were then removed under reduced pressure by means of a water aspirator and then the residue was subjected to a partial vacuum, for example, an oil vacuum pump. The resulting white appearing solid residue was triturated with ether (3 triturations of 250 ml. each). The ether acts as a solvent for removing certain impurities and was removed by decantation, any residual ether being removed under partial pressure.

Hot chloroform was then used to extract 1-(tetrahydro - 2-furanyl) - 5-fluorouracil from the solid residue. Three extractions with 700 ml. portions of hot chloroform has been found adequate although the number of extractions necessary to extract all of the 1-(tetrahydro - 2-furanyl) - 5-fluorouracil will vary with the temperature of the hot chloroform. It is suggested that any remaining solid be checked by conventional thin layer chromatographic techniques to determine the completeness of the extraction.

The combined chloroform extracts were evaporated to dryness under reduced pressure to leave a white solid residue. The white solid residue was then dissolved in boiling ethanol. The ethanol solution was allowed to cool to about 5°C and stand at about 5°C to give crystalline white needles. The resulting solid represented 615 grams of product which had a melting point of 169° to 170°C and represented a yield of 80%. The calculation of theoretical yield was based on the amount of 5-fluorouracil used as starting material.

The invention may be embodied in other specific forms without departing from its spirit or essential characteristics. The described embodiment is to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An improved method for synthesizing 1-(tetrahydro-2-furanyl-5-fluorouracil comprising the steps of:
    reacting a solution of the bis-trimethylsilyl derivative of 5-fluorouracil with 2-chlorotetrahydrofuran in a reaction vessel in the presence of a solvent comprising methylene chloride and 4 A molecular sieves;
    removing water and HCl from the reaction solution with the molecular sieves and thereafter removing the molecular sieves from the reaction solution;
    precipitating 1-(tetrahydro-2-furanyl)-5-fluorouracil from the solution by suitably maintaining the pH of the solution above at least 7.5;
    separating the precipitate from the solution; and
    concentrating and purifying the precipitate.

2. A method as defined in claim 1 wherein said reacting step comprises maintaining said reaction vessel and the contents thereof at a temperature within the range of about −65°C to the freezing point of the solvent.

3. A method as defined in claim 1 wherein said precipitating step comprises slowly combining the reaction solution to a basic solution of ammonium hydroxide and methanol to form a combined mixture.

4. A method as defined in claim 3 wherein said precipitating step further comprising removing heat generated by the exothermic reaction of said precipitating step and keeping the temperature of said combined solutions within the range of about −10°C to −78°C until all of said reaction solution has been added to said basic solution and thereafter warming said combined solution to room temperature.

5. A method as defined in claim 1 comprising the steps of flushing said reaction vessel with a dry, inert gas during said reacting, removing and precipitating steps.

6. A method as defined in claim 1 wherein said reacting step comprises preparing said bis-trimethylsilyl derivative of 5-fluorouracil by the steps of reacting 5-fluorouracil with hexamethyldisilazane at reflux temperature and volatilizing remaining liquid therefrom.

7. A method as defined in claim 1 wherein said precipitating step includes adjusting the pH of said solution with an acid.

8. An improved method of synthesizing 1-(tetrahydro-2-furanyl)-5-fluorouracil comprising the steps of:
preparing a first reactant by placing a silylated derivative of 5-fluorouracil, bis-trimethylsilyl-5-fluorouracil, in a reaction vessel with a first mixture of a solvent comprising methylene chloride and 4 A molecular sieves;

stirring the contents of said reaction vessel while chilling the same to a temperature below about −65°C;

preparing a second reactant by mixing 2-chlorotetrahydrofuran with a second mixture of a solvent comprising methylene chloride and 4 A molecular sieves and chilling the same to a temperature within the range of about −65°C to the freezing point of the solvent and thereafter adding the same to said first reaction mixture by dropwise addition to the reaction vessel while maintaining the temperature of the contents of the reaction vessel within the range of about −65°C to the freezing point of the solvent; and removing water and HCl from the reactant mixtures with the molecular sieves.

* * * * *